United States Patent [19]

Switalski et al.

[11] Patent Number: 5,536,664
[45] Date of Patent: Jul. 16, 1996

[54] METHOD FOR QUANTITATIVE NIR SPECTROSCOPIC ANALYSIS

[75] Inventors: Steven C. Switalski; Thomas R. Kissel, both of Rochester, N.Y.

[73] Assignee: Johnson & Johnson Clinical Diagnostics, Inc., Rochester, N.Y.

[21] Appl. No.: 437,734

[22] Filed: May 9, 1995

Related U.S. Application Data

[62] Division of Ser. No. 381,629, Jan. 31, 1995, which is a division of Ser. No. 267,086, Jun. 27, 1994.

[51] Int. Cl.⁶ ................................. G01N 21/62
[52] U.S. Cl. ................ 436/171; 436/63; 422/82.05
[58] Field of Search .................... 250/339.11, 341.8; 422/82.05, 68.1, 55, 56; 436/164, 171

[56] References Cited

U.S. PATENT DOCUMENTS

| | | | |
|---|---|---|---|
| 3,992,158 | 11/1976 | Przybylowicz | 23/253 |
| 4,258,001 | 3/1981 | Pierce | 422/56 |
| 4,357,363 | 11/1982 | Pierce | 427/2 |
| 4,381,921 | 3/1983 | Pierce | 436/535 |
| 4,582,684 | 4/1986 | Vogel et al. | 422/57 |
| 5,068,536 | 11/1991 | Rosenthal | 250/341 |
| 5,197,470 | 3/1993 | Helfer et al. | 128/634 |

FOREIGN PATENT DOCUMENTS

| | | | |
|---|---|---|---|
| 525550 | 7/1992 | European Pat. Off. | 33/52 |
| WO93/00580 | 1/1993 | WIPO | 21/35 |

OTHER PUBLICATIONS

Heise et al. AN 94338279 Medline Abstract.
Marquardt AN 94121233 Medline Abstract.
Robinson AN 92405382 Medline Abstract.
Maier AN 1995:460235 Hcaplus Abstract.

*Primary Examiner*—Lyle A. Alexander
*Attorney, Agent, or Firm*—Dana M. Schmidt

[57] ABSTRACT

There is disclosed a slide test element and method of assay that allows for detection of analytes in biological liquids without the use of any detection reagents. The method uses NIR spectroscopy and a test element comprising a support, and a substantially constant light-path defining layer comprising a diffusely-reflecting material that is a) sufficiently porous in all directions as to allow a liquid to spread uniformly in all directions, and b) homogeneously reflects at least 95% of NIR radiation.

2 Claims, 5 Drawing Sheets

METHOD FOR QUANTITATIVE NIR SPECTROSCOPIC ANALYSIS

This is a divisional of Ser. No. 08/381,629, filed on Jan. 31, 1995 which is a Divisional of application U.S. Ser. No. 08/267,086, filed Jun. 27, 1994.

FIELD OF INVENTION

This invention relates to the assaying of biological liquids for analytes using NIR spectroscopy and a dried slide test element.

BACKGROUND OF THE INVENTION

For the last 11 years or more, the conventional dried reagent approach to clinical chemistry (which does not use liquid or reconstituted liquid reagents in a cuvette) has been the dried slide test element technology such as that used by Eastman Kodak Company under the trademark "Ektachem" slides. In such technology, a dried reagent is supplied along with a binder in a reagent layer on a slide-like element. To assist in spreading the liquid uniformly into an area that then flows into the reagent layer, a spreading layer is usually provided above the reagent layer, for example, that taught in U.S. Pat. No. 3,992,158. However, the reading of the elements is via reflectance from the opposite side, and every effort is made to keep the detection light from penetrating the spreading layer, since the detectable color change occurs in the reagent layer(s).

Although such test elements work admirably, as evidenced by the billions of slide elements sold since Eastman Kodak introduced the product, it would be advantageous to provide a dried test element that does not require the various reagents required in, e.g., the aforesaid '158 patent and the related test elements.

Some efforts have been made to develop spectroscopic analysis of liquids into a quantitative science. Attempts were made to use impervious supports on which a liquid sample is spread. However, for quantitative analysis of most biological liquids, this is unsatisfactory since the constancy of the light-path as required by Beer's law cannot be easily maintained on an impervious support. A similar objection exists for early pervious supports that were tried, e.g., paper and thin layer chromatography elements. That is, although the depth of the liquid scanned is more maintainable in such pervious supports, they lack uniform three-dimensional porosity since the liquid does not spread uniformly in all directions throughout a known volume.

The most recent attempt at spectroscopic analysis is the use of microporous polymers to create a porous sheet for IR spectroscopy, for example, as taught in WO 93/00580. Although this purports to provide for wavelengths of detection that cover NIR as well as IR (p. 1, lines 25–28), where NIR as used therein is from about 750 nm to about 3000 nm, in fact the rest of the teaching is for IR only (above 3000 nm). The reason is, that it is known in the literature that the sheet materials listed in WO 93/00580 are unable to function quantitatively in the NIR, particularly in the reflective mode where the sheet must be at least 95% reflective. All of those materials listed (polyethylene, polypropylene, poly(tetrafluoroethylene) (PTFE), ethylene/propylene copolymers, poly(vinyl fluoride), polyester, chlorotrifluoroethylene polymer, and Nylon), with the exception of PTFE, are not at least 95% reflective. PTFE does not however have the porosity required—it is not "sufficiently porous" as set forth in the Summary hereinafter.

SUMMARY OF THE INVENTION

We have discovered a microporous material that avoids the problems noted above.

More specifically, in accordance with one aspect of the invention, there is provided a test element for analyzing analytes in patient samples, comprising
a support, and
a substantially constant light-path defining layer comprising a diffusely-reflecting material that is a) sufficiently porous in all directions as to allow a liquid to spread uniformly in all directions, and b) homogeneously reflects at least 95% of NIR radiation,
the element being substantially free of:
i) reagents capable of reacting with the analyte, and
ii) a hydrophilic polymer layer that a) is separate from the light-path defining layer, and b) has a thickness equal to or greater than 1 micron.

In accordance with another aspect of the invention, there is provided a method of quantitatively analyzing an analyte of a biological sample by near infrared (NIR) reflective or scattering spectroscopic quantitative analysis, comprising the steps of
a) placing an aliquot of sample onto a test element comprising
a support, and
a substantially constant light-path defining layer comprising a diffusely-reflecting material that is a) sufficiently porous in all directions as to allow a liquid to spread uniformly in all directions, and b) homogeneously reflects at least 95% of NIR radiation,
b) illuminating the sample within the sheet with light of NIR wavelengths,
c) detecting light of such wavelength that is reflected or scattered by the sheet, and
d) spectroscopically analyzing the detected light for signals that are characteristic of the analyte being analyzed.

DESCRIPTION OF THE PREFERRED EMBODIMENT

This invention is based on the discovery that the spreading layer described in the aforesaid '158 patent is ideally suited for quantitative NIR spectroscopic analysis, when it comprises the light-path defining layer, unlike the construction in the '158 patent.

Figure 1:
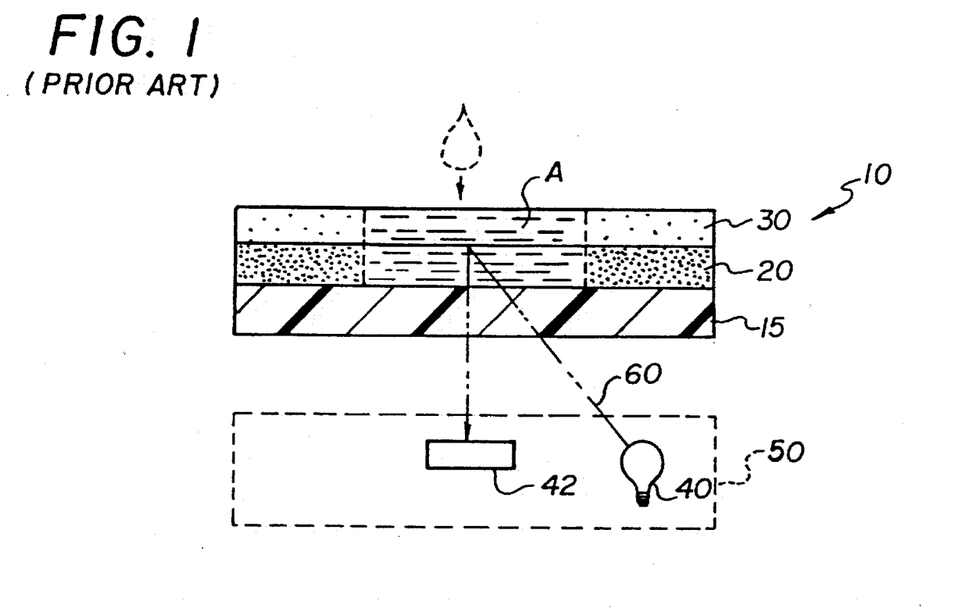
FIG. 1 is a schematic section view of a prior art test element with dried reagents, and the method used to analyze for the analyte of choice.

Referring to FIG. 1, the conventional slide element 10 taught by the '158 patent comprises a transparent plastic support 15, one or more reagent layers 20, and a uniformly porous spreading layer 30. Layer 30 provides for uniform spreading of a drop of sample (shown in phantom) into a volume of dispersed area A in layer 30 (shown with liquid), which then migrates downward into reagent layer 20. (The reagents of layer 20 are indicated by a heavier stipple.) Importantly, the element is read from the opposite side for reflectance, using a light source 40 and a detector 42 in a reflectometer 50. The spreading layer, in turn, is provided with a screen material to make it reflective, such as, by incorporating $TiO_2$. As a result, the light-path 60 is ideally defined by only layers 15 and 20 and not by the spreading layer, so as to detect a color change in layer 20. (Although some examples of "Ektachem"® brand slides made in accordance with the teaching of the '158 patent may in fact have some light transmitted into the spreading layer, it is shown below that many "Ektachem" slides in fact have less than 1% of the light-path operationally defined by that layer, that is, within the normal operating range of the slide. In any event, such slides have always been taught for use with detection reagents.)

Our invention is based on the discovery that the spreading layer by itself makes an excellent porous sheet for conducting quantitative NIR spectroscopic analysis, when the light-path is in fact defined by the spreading layers rather than any adjacent layers. The reason is that the sufficiently porous nature of the spreading layer makes it ideal for providing a constant predictable path length of light during the period of use, unlike the binders used in the reagent layers of FIG. 1 that define the light-path within that slide element.

As used herein, "NIR" spectroscopy or radiation means, using the wavelengths of from about 750 to about 3000 nm. "Substantially constant light-path" means, with deviations of no more than about 1%. "Quantitative" means, measurement of actual quantities based upon accuracy and precision that is acceptable in a clinical laboratory.

"Sufficiently porous" means, in all directions so that a liquid spreads within the layer uniformly in all directions. As noted, this latter is a property already known to exist in the spreading layer of the element taught in the '158 patent. Hence, the most preferred level of "sufficient porosity", as used herein, is any layer of material that is as porous in all directions as the spreading layers of the '158 patent. The $TiO_2$ layer of Ex. 1 that follows is a satisfactory example thereof.

To test for other materials having suitable porosity, a useful procedure is that set forth in col. 6, line 22 to col. 7, line 7 of the aforesaid '158 patent which is expressly incorporated herein by reference. However, volumetric and thickness requirements set forth therein need not be followed, nor must a gelatin sublayer be used. Alternatively, the gelatin can be used since this is just a test for porosity.

Thus it will be readily apparent that the basic components of this invention are conventional: the components and construction of the test element light-path defining layer(s), and the NIR analysis for detection of signal peaks representative of certain analytes, e.g., total protein, glucose, total cholesterol, albumin, globulin, triglycerides, urea, creatinine, HDL, and LDL.

The invention resides in the discovery that the test element of the '158 patent, when properly constructed with substantially no reagents and without the reagent layer, will allow adequate quantitative detection of analytes in biological liquids using NIR spectroscopy. For these reasons, except as stated herein, details are not provided for the construction of the test element or the conduction of NIR analysis, as such are well known to those skilled in the respective art. (Representative useful peaks for, e.g., total protein, include 2050, 2160, 2170, and 2180 nm, as is well-known.)

Although the description herein is of preferred embodiments featuring reflective NIR assays, using the spreading layer of U.S. Pat. No. 3,992,158, the invention is not limited thereto. It is also useful with scattering-type NIR analysis, and with a light-path defining layer of some other material having the same NIR capabilities and porosity as noted above in the Summary.

Figure 2:
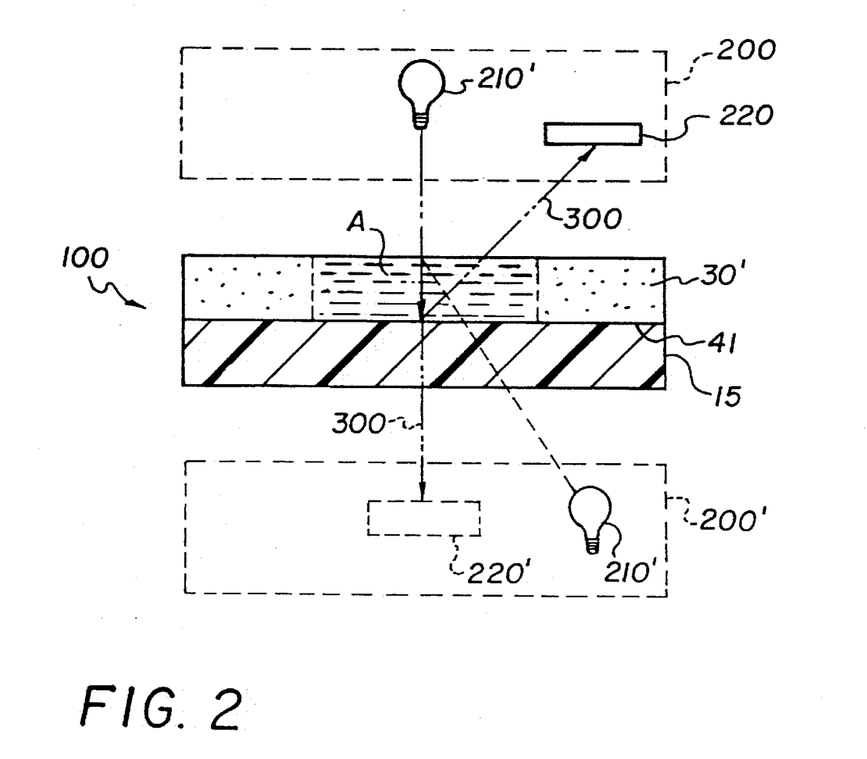
FIG. 2 is a schematic view similar to that of FIG. 1, but of the invention.

The preferred slide test element is element 100, FIG. 2. This preferably comprises a layer 30' that is substantially the same as any of the spreading layers of the aforesaid '158 patent, provided that it is free of detection reagents. Optionally it is attached to NIR-transparent plastic support 15 by a thin conventional subbing layer 41, or by corona-treating or plasma-treating the support. Supports described in the '158 patent are useful. "Thin" as used herein for the subbing layer means, a thickness less than 1 micron, since greater thicknesses tend to interfere with the NIR reflection, especially if the subbing layer comprises a hydrophilic polymer.

Alternatively, if the composition of layer 30' is self-adhering to layer 15, layer 41 can be omitted.

Detection of analytes in a liquid deposited in area A is by a conventional spectrophotometer 200, using an appropriate NIR energy source 210 and an NIR detector 220. (Although a preferred mode of analysis is from the front-side as shown, it can also be from the back side, shown in phantom.)

As is known from the '158 patent, preferred materials for use in layer 30' of element 100 are selected from the group consisting of a blush polymer, microcrystalline particles, and adhered particles, all with or without reflective pigments present.

When doing the NIR analysis from the top side of test element 100, layer 41 optionally includes a mirrored surface, which can be provided in the form of a metallized layer, a thin particulate ceramic layer, a fine metal oxide, or metal dispersed in a transparent polymer. This enhances the reflection of path 300, since without the mirrored surface, the NIR energy from source 210 is more likely to be partially absorbed at or near layers 41 and 15.

Figure 3:
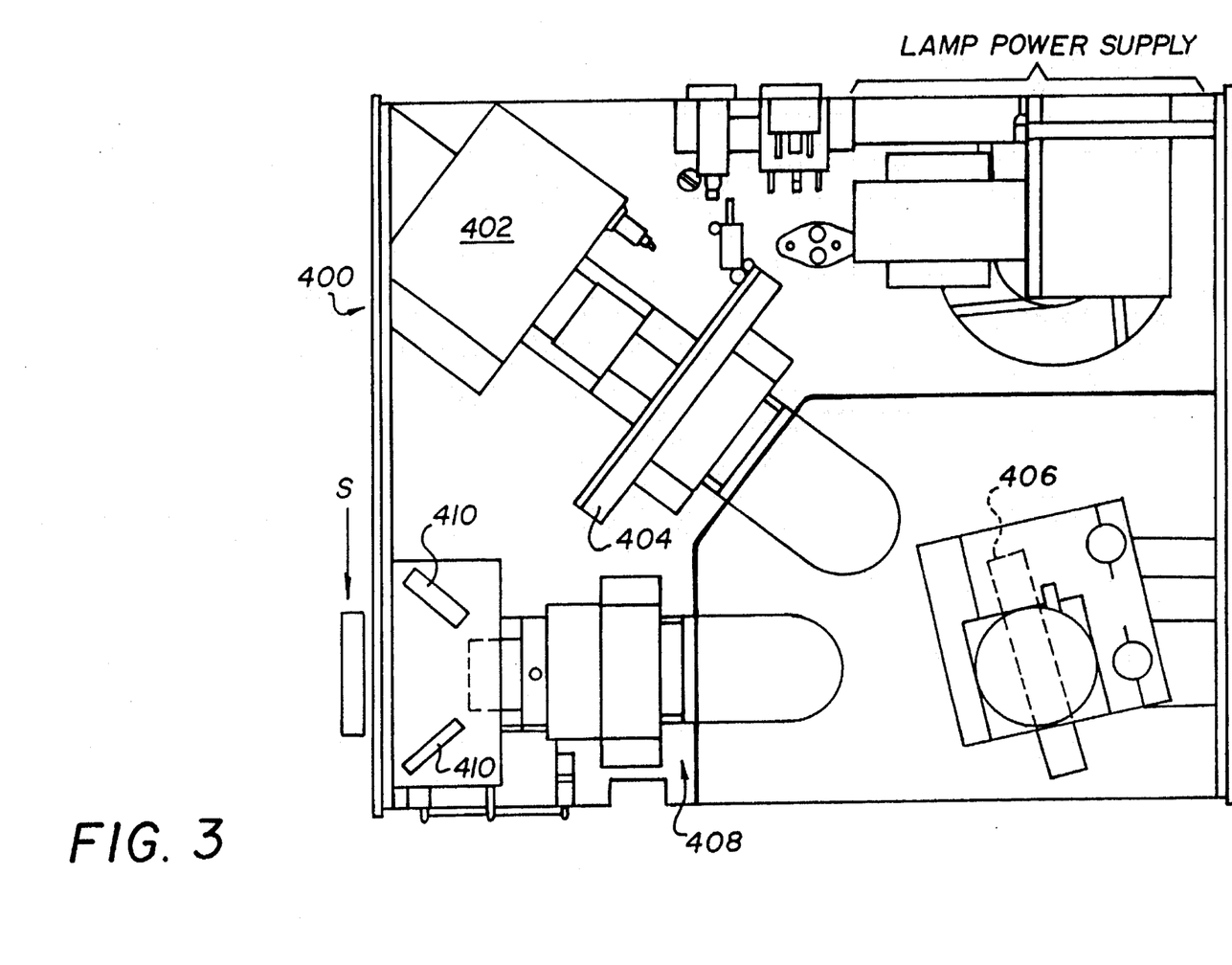
FIG. 3 is a partially schematic plan view of a useful spectroscope.

As noted, the NIR analysis is conventional. In brief, it is done as follows:

A slide element is attached to a support and placed in the position shown as "S" in FIG. 3. A spectrum of the slide is collected using conventional spectrometer 400 and wavelengths generated by light source 402, chopper 404, monochromator grating 406, focusing lenses 408, and detectors 410. The wavelengths are selected from the full spectrum from 1200 to 2400 nm to achieve a blank reading. The element is then removed from the spectrometer and spotted with the liquid to be assayed, in a preferred amount, such as 300 microliters. The liquid is allowed to spread into the slide for about 30 to 90 sec. and the slide then returned to the spectrometer. A new spectrum of the slide and liquid is generated and collected using spectrometer 400. The results are then analyzed using the 2nd derivative of the absorbance followed by multiple linear regression (MLR) to discriminate the analyte from background. Further details are shown in the following examples.

EXAMPLES

The following examples are illustrative only, and are not an exhaustive list of the embodiments of the invention.

In the following examples, the slide test element had the following construction:

---

(top layer)

TiO₂ or BaSO₄
Cellulose Acetate
(subbing layer)

Binder = poly(vinyl pyrrolidone)
(Coverage = less than or = 1 mg/cm²)
poly(ethylene terephthalate)
support

---

The protein examples which follow were calibrated and read at 2057.5 nm and 2180.5 nm light. Additionally, however, the regions 2050–2250 nm and/or 1500–1800 rum are also useful. The spectroscope used was a "Quantum 1200 Plus" (TM) spectroscope available from LT Industries, schematically shown in FIG. 3. The 2nd derivative of the absorbance followed by multiple linear regression (MLR) was used to discriminate the analyte from background. The second derivative is preferred because it removes nonchemical differences such as baseline shifts and instrument noise, and enhances shoulders and inflections of the curves of the raw absorption spectra. See, e.g., U.S. Pat. No. 5,197,470 for an example of the process used herein. Alternatively, principal component analysis and/or regression and/or partial least squares can be substituted for the multiple linear regression analysis.

EXAMPLE 1

Total Serum Protein On A TiO₂ Slide

Figure 4:
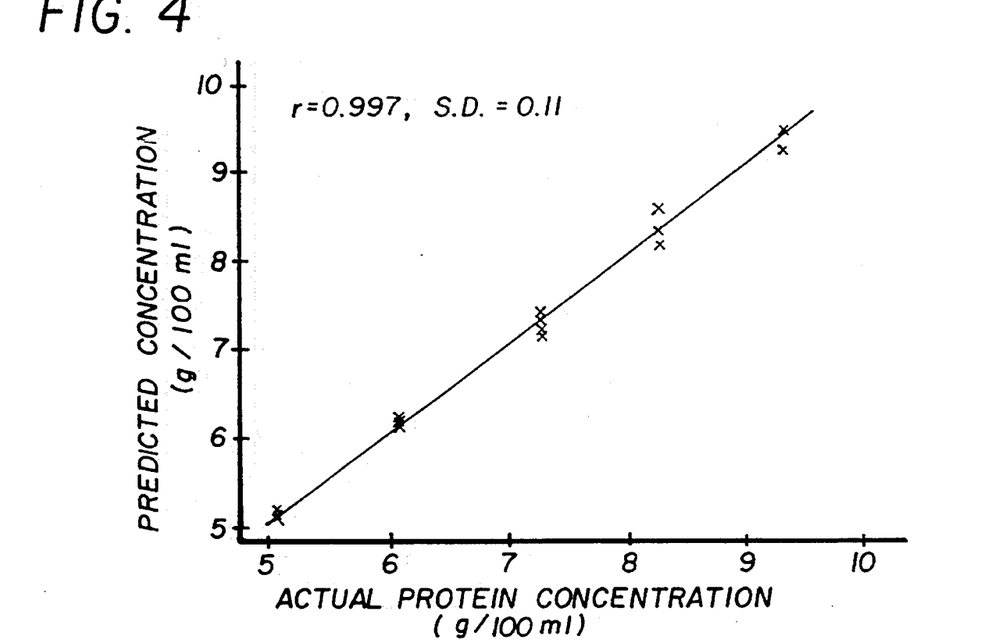
FIGS. 4–7 are plots of actual analyte concentration versus predicted concentration resulting from the use of the invention.

The slide construct shown above using a 2–6 mil thick TiO₂ matrix at a coverage of 1–6 g/m squared, was spotted with 300 μL of a calibrator fluid spiked with amounts of total protein that are on the horizontal axis of FIG. 4. The spectroscopic readings were processed so that the MLR predictions are plotted, FIG. 4, on the vertical axis, and the a priori actual values plotted on the horizontal axis, yielding an r value, where "r" is the regression correlation value, of 0.997 and a standard deviation of 0.11. Clearly, this result is well within laboratory standards of a quantitative assay.

These results also constitute the calibration curve used with subsequent examples.

EXAMPLE 2

Total Serum Protein On A TiO₂ Slide

Figure 5:
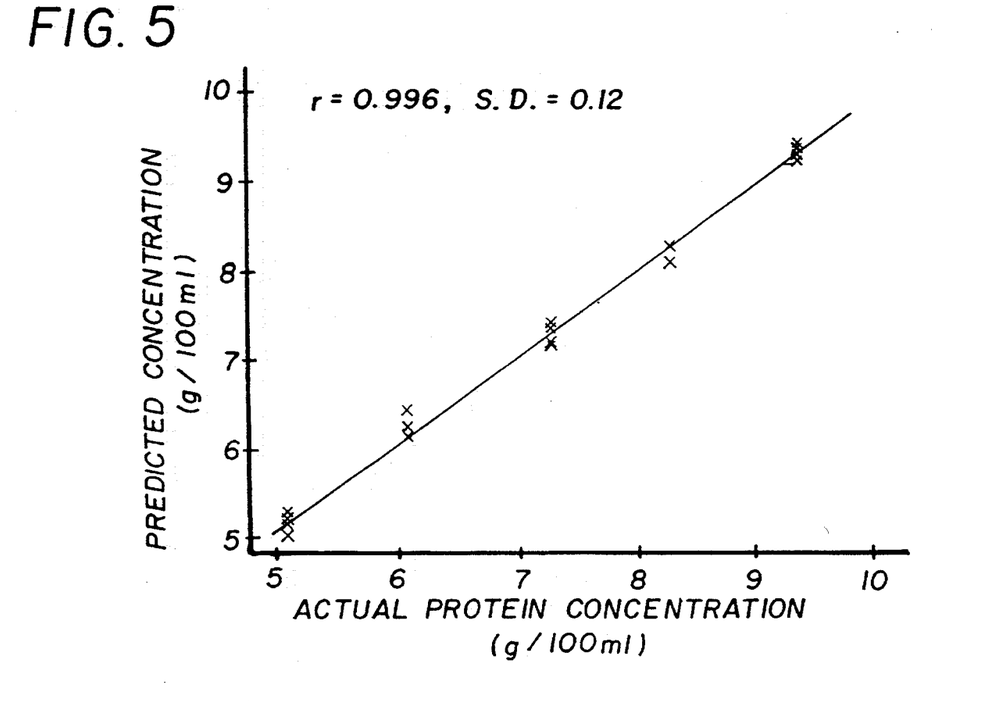

The experiment of Example 1 was repeated, except that the calibration curve of FIG. 4, Example 1, was used to assay other known concentrations of analyte not used in preparing the calibration curve of Ex. 1. The results are plotted in FIG. 5. The "r" value was 0.996 and the standard deviation, 0.12, indicating that the results of Ex. 1 could be used as a calibration curve with "unknowns".

EXAMPLE 3

Total Cholesterol on a BaSO₄ Slide Test Element

Figure 6:
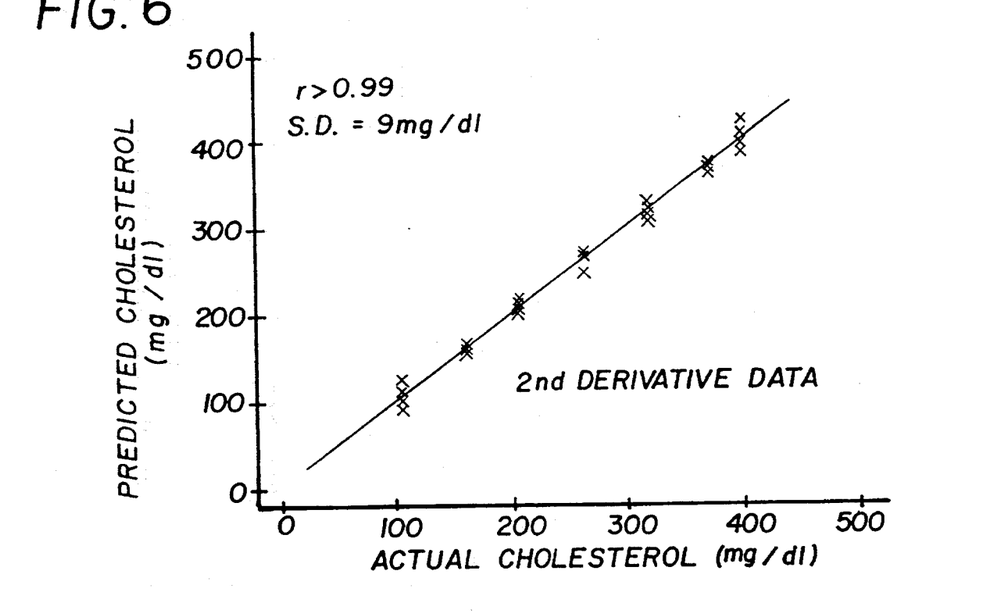

The experiment of Ex. 1 was repeated, except that the light-path defining layer (other than the support) comprised BaSO₄ at 1 to 6 g/cm² coverage, instead of TiO₂. The calibrators had spiked in the levels of cholesterol listed on the horizontal axis of FIG. 6. The predicted values obtained spectroscopically were those plotted on the vertical axis, producing a result of r=0.99 and a standard deviation of 9 mg/dl, which is well within acceptable limits for this concentration range of cholesterol.

EXAMPLE 4

Total Cholesterol on a BaSO₄ Slide Test Element

Figure 7:
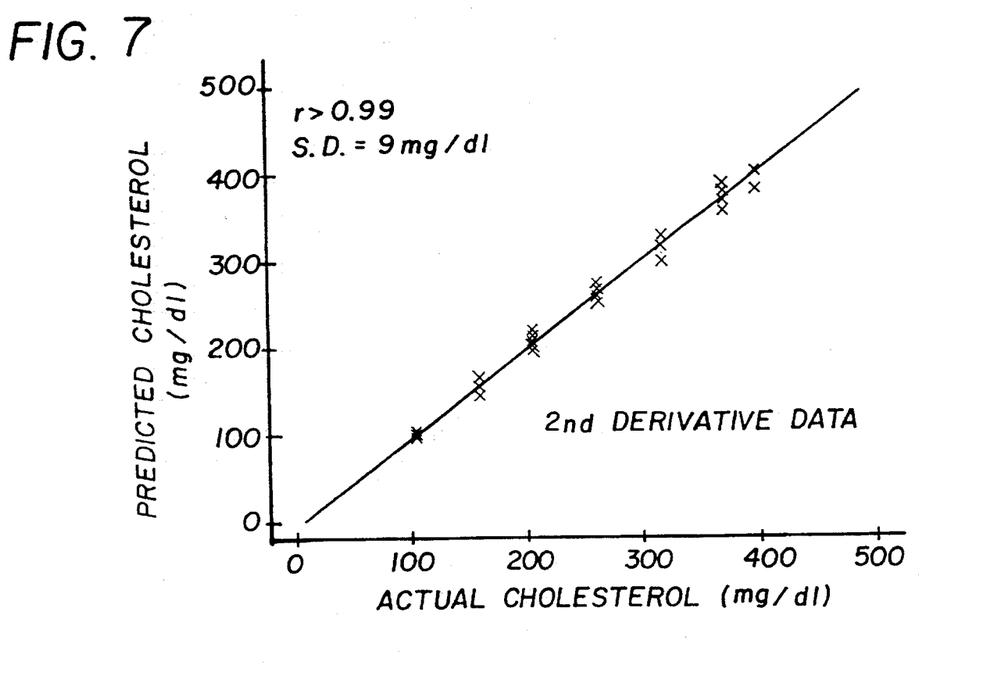

Example 2 was repeated, except that the assay was for total cholesterol, using the calibration curve generated in Ex. 3. The results appear in the plot of FIG. 7, with r values and a standard deviation identical to that of FIG. 6.

COMPARATIVE EXAMPLE NO. 1

Figure 8:
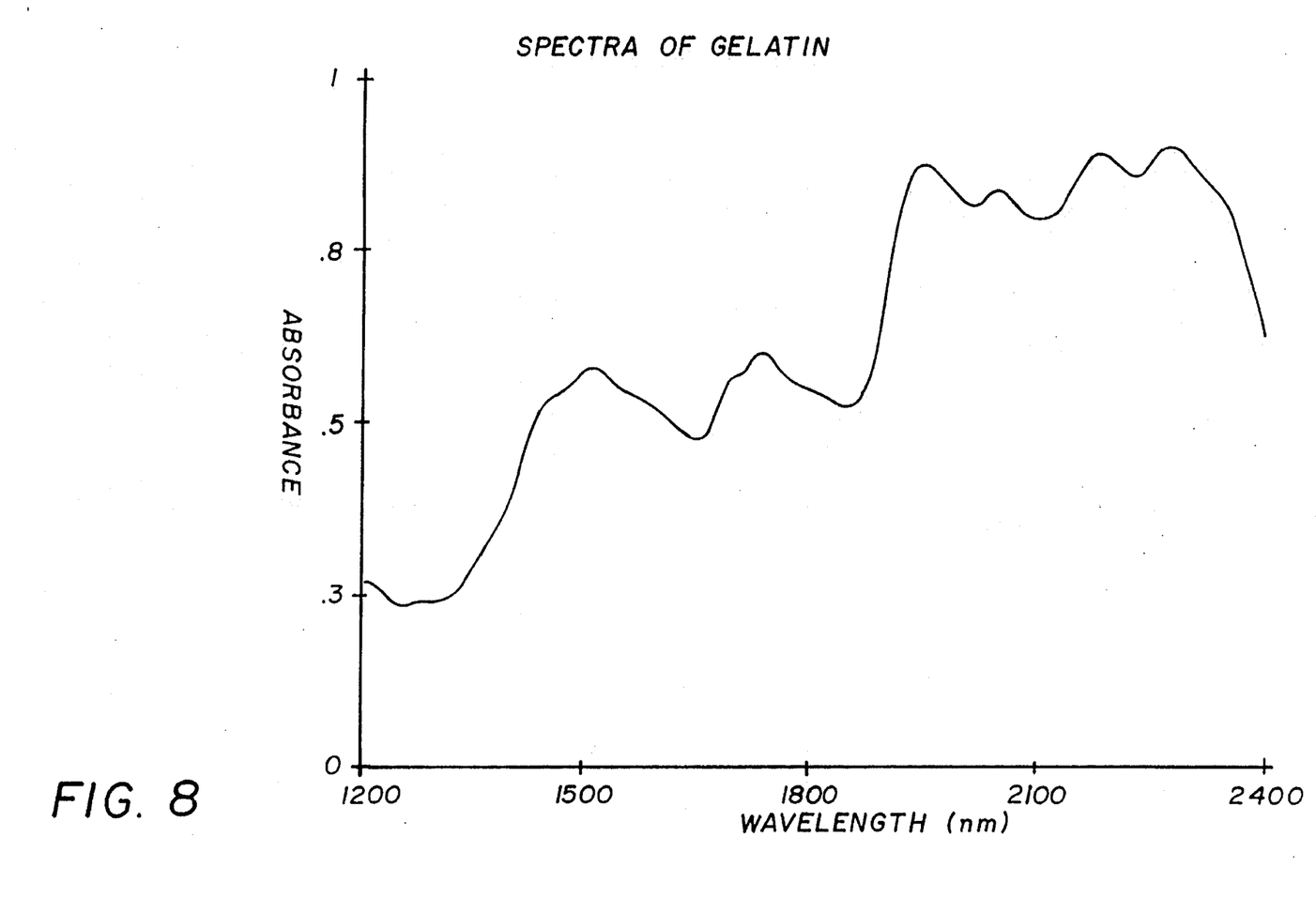
FIG. 8 is the absorption plot of gelatin at NIR wavelengths, showing why gelatin is unacceptable in significant thicknesses in the light-path defining layers of the test element.

FIG. 8 is included solely to demonstrate that any substantial thickness [greater than 1 micron] in the slide test element comprising gelatin, will not be reflective of at least 95% of NIR radiation. The reason of course is due to the substantial absorption occurring particularly from 1500 nm to 2400 nm, a major portion of the NIR range of the invention. (The type of gelatin is of no consequence in this regard.) Hence, gelatin is to be eschewed, at least in thicknesses ≧1 micron.

COMPARATIVE EXAMPLE NO. 2

To demonstrate that the conventional "Ektachem" (TM) slide for, e.g., glucose, does not permit passage of the reflectometer light into the spreading layer for ranges of analyte for which the slide is intended, such a glucose slide was tested in a conventional Perkin Elmer "Lambda Nine" (TM) spectrometer with a known concentration of glucose. The peak absorbance of the dye was 1.22 absorbance units which is approximately a 7% transmission, so that the light contributed by reflectance within the spread layer (above that dye layer) is 0.07×0.07=0.0049, or only 0.3% to 0.5% of the signal, instead of the required at-least 95%. That is, the conventional "Ektachem" slide is not designed to transmit light into and through the spreading layer at the ranges of analyte concentration intended for use.

The invention has been described in detail with particular reference to preferred embodiments thereof, but it will be understood that variations and modifications can be effected within the spirit and scope of the invention. For example, the disclosed features can also be used in the absence of any unnamed parts, so that it can consist essentially of only the items disclosed.

What is claimed is:

1. A method of quantitatively analyzing an analyte of a biological sample by near infrared (NIR) reflective or scattering spectroscopic quantitative analysis, comprising the steps of:

a) placing an aliquot of sample onto a test element comprising, in overlying relation,
   a support, and
   a substantially constant light-path providing layer consisting essentially of a diffusely-reflecting material that i) is sufficiently porous in all directions as to allow a liquid to spread uniformly in all directions, and ii) homogeneously and diffusively reflects at least 95% of NIR radiation, b) illuminating the sample within said test element with light of NIR wavelengths, c) detecting light of such wavelength that is reflected or scattered by said test element, and d) spectroscopically analyzing the detected light for signals that are characteristic of the analyte being analyzed, said test element being substantially free of reagents during said steps a)–d).

2. A method as defined in claim 1, wherein said step d) comprises comparing said signal against a calibrated model for the analyte of choice based on either the raw detected signal or derivatives thereof, to ascertain from said calibrated model the concentration of said analyte of choice.

* * * * *

UNITED STATES PATENT AND TRADEMARK OFFICE
CERTIFICATE OF CORRECTION

PATENT NO. : 5,536,664
DATED : July 16, 1996
INVENTOR(S) : Steven C. Switalski
Thomas R. Kissel It is certified that error appears in the above-indentified patent and that said Letters Patent is hereby corrected as shown below:

Figure on title page,
In the upper box labeled "200", delete "210'" and insert therefor --210--.

Sheet 1 of 5, Fig. 2
In the upper box labeled "200", delete "210'" and insert therefor --210--.

Signed and Sealed this

Twenty-eighth Day of January, 1997

Attest:

BRUCE LEHMAN

Attesting Officer        Commissioner of Patents and Trademarks